Figure 1:
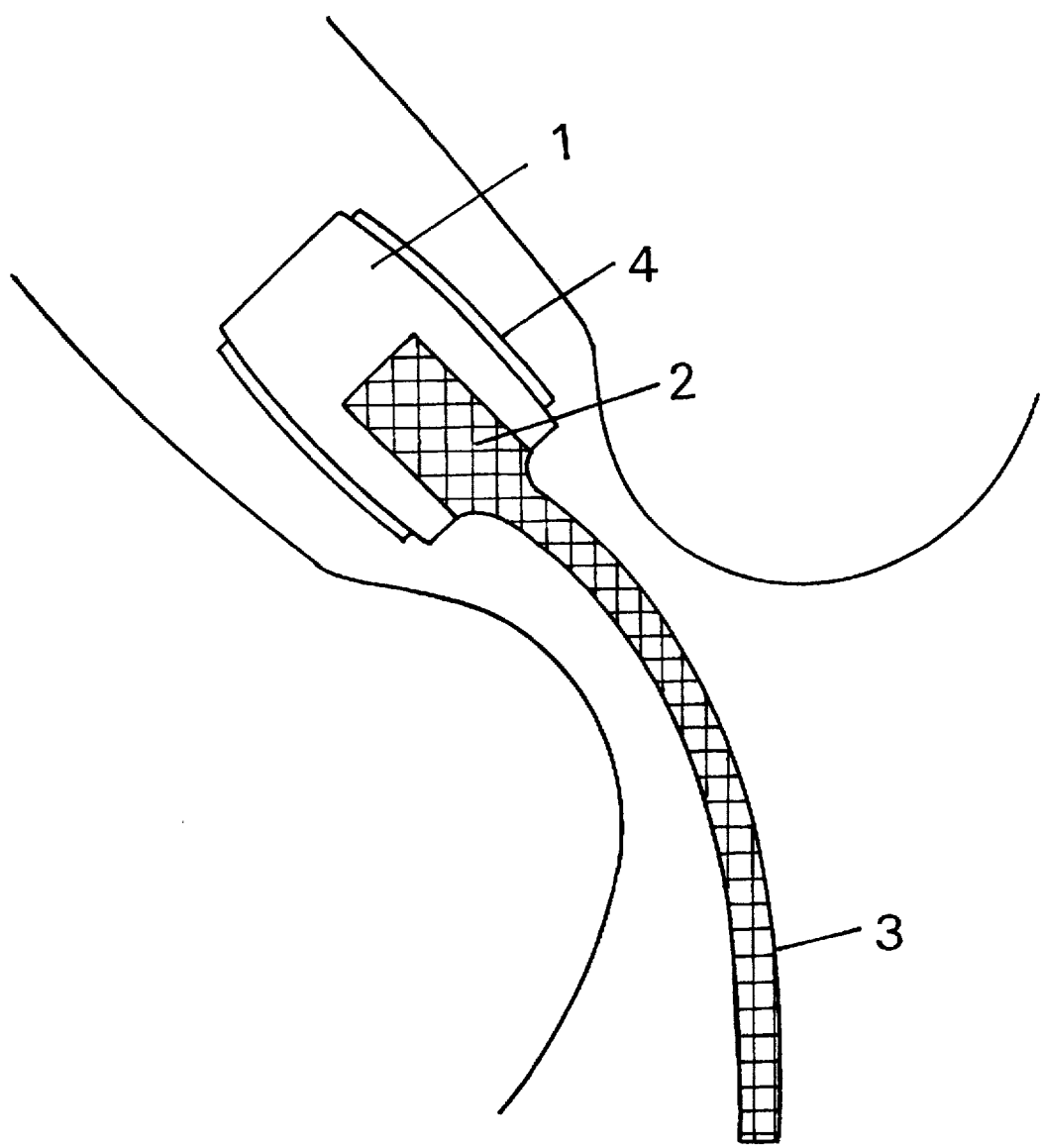

United States Patent [19]

Kollerup et al.

[11] Patent Number: 5,800,338

[45] Date of Patent: Sep. 1, 1998

[54] TAMPON OR CLOSURE DEVICE FOR BODY PASSAGEWAYS OF ANIMAL OR HUMAN BEINGS

[75] Inventors: Ib Kollerup, Espergærde; Erik Ethelfeld, Copenhagen, both of Denmark

[73] Assignee: Coloplast A/S, Espergaerde, Denmark

[21] Appl. No.: 727,405

[22] PCT Filed: Apr. 12, 1995

[86] PCT No.: PCT/DK95/00155

§ 371 Date: Oct. 17, 1996

§ 102(e) Date: Oct. 17, 1996

[87] PCT Pub. No.: WO95/28138

PCT Pub. Date: Oct. 26, 1995

[30] Foreign Application Priority Data

Apr. 18, 1994 [DK] Denmark ............ 0445/94

[51] Int. Cl.⁶ ........................................... A61F 2/00
[52] U.S. Cl. .................. 600/29; 600/32; 604/904; 604/358
[58] Field of Search ................. 604/904, 358; 600/29, 30, 32

[56] References Cited

U.S. PATENT DOCUMENTS

| | | |
|---|---|---|
| 1,561,020 | 10/1925 | Pond . |
| 1,731,665 | 10/1929 | Huebsch . |
| 3,520,302 | 7/1970 | Jones . |
| 3,916,898 | 11/1975 | Robinson . |
| 4,351,339 | 9/1982 | Sneider ............ 604/904 |
| 4,979,947 | 12/1990 | Berman . |
| 5,509,427 | 4/1996 | Simon et al. ............ 600/29 |

FOREIGN PATENT DOCUMENTS

| | | |
|---|---|---|
| 788407 | 1/1958 | United Kingdom . |
| 2153686 | 8/1985 | United Kingdom . |

*Primary Examiner*—Jennifer Bahr
*Assistant Examiner*—Rosiland Kearney
*Attorney, Agent, or Firm*—Ostrolenk, Faber, Gerb & Soffen, LLP

[57] ABSTRACT

A tampon or closure device for insertion into an external opening of an artificial or natural body canal of an animal or human being includes a resilient compressed plug-like body of a molded material, the body having a longitudinal direction and being expandable to a cross-sectional dimension ensuring closure of the body canal when inserted in the opening with the longitudinal direction extending longitudinally in the canal. The body is provided with a withdrawal handle element protruding from the body and connected with an anchor part encapsulated in the body and having a relatively large bearing face against the surrounding molded material of the body. The handle element and anchor part are made from a material with a knitted structure to provide a 3-dimensional bond to the molded material of the body where the anchor part is designed as a soft flexible element oriented in the longitudinal direction.

8 Claims, 2 Drawing Sheets

TAMPON OR CLOSURE DEVICE FOR BODY PASSAGEWAYS OF ANIMAL OR HUMAN BEINGS

The invention relates to a tampon or closure device for insertion into externally debouching. artificial or natural body canals of animal or human beings and comprising an resilient compressible plug-like body of moulded material, which body when inserted is expanded to a cross-sectional dimension ensuring closure of the body cavity (canal) in question, and which body for use at withdrawal from the body canal is provided with a handle means protruding from the body and being in connection with an anchor part encapsulated in the body with a relatively large bearing face against the surrounding moulded material and made from a material with a knitted structure providing for a three-dimensional bond to the moulded material.

In GB patent no. 788,407, GB patent application no. 2,153,686 and the U.S. Pat. Nos. 1,561,020, 1,731,665, 3,520,302, 3,916,898 and 4,979,947, among others, are disclosed various forms of tampons for placement in externally debouching body canals, eg. vagina or anus, for absorption of fluids and/or for medication.

From the mentioned publications is further known to provide devices of this type with a protruding handling means for use at withdrawal from the body canal in question, most frequently being in the form of a cord fastened to the tampon and extending in the longitudinal direction hereof.

By way of example, from GB patent application no. 2,153,686 and the U.S. Pat. Nos. 3,916,898 and 4,979,947 is it known to design devices of the type in question from a spongy or plastic foam material, eg. polyurethane foam, and having a handle means in the form of a relatively thin cord or string, eg. from a monofilament material which is lead through the material, maybe in the form of a loop.

Since such a cord or string must per se have sufficiently strength in order not to break during the withdrawal. it has, however, appeared that in connection with tampons of plastic foam material which in the expanded state may be relatively weak, there is a considerable risk that the cord is pulled out of the tampon or the closure device without it following or the material breaking such that a part of the closure device remains in the body canal in question and thus may constitute a considerable risk of infection.

From international patent application WO 88/05294 is known an anal plug of the initially indicated type and made from plastic foam material, where a protruding handle cord is connected with a separate disc-shaped intermediate piece disposed across the longitudinal direction of the device.

The intermediate piece may be of a perforated or knitted tissue with cords fastened to a rigid anchor part which is anchored in the tissue. In this known device the anchoring device thus comprises several parts which makes the plug complicated and dearer.

For a tampon or closure device of the indicated type, the above stated drawbacks are avoided according to the invention in the way that the anchor part is designed as a stocking-like element orientated in the longitudinal direction of the plug-like body and is in integrated connection with a handle means.

Besides, a processing step is saved, the withdrawal device being encapsulated at the same time as the moulding of plugs contrary to conventional manufacture where the withdrawal device is not fastened to the plug until this is moulded.

As a consequence of the relatively large bearing face and the three-dimensional bond to the moulded material in the plug-like body, it has even by manufacture hereof from a relatively weak or brittle material proved to be possible to obtain such a secure attachment of the handle means that the risk of tearing the closure device during withdrawal is eliminated or at least reduced considerably.

The anchor part may be manufactured from a soft flexible material, eg. in the form of relatively fine-meshed netting. A preferred embodiment is characterized in that the anchor part is designed as a relatively short element of woven or non-woven material, preferably fabric or plastic, eg. gauze.

The manufacture can be expedient in that one end of the anchor part, which is designed as a stocking and integrated with the handle part meant to protrude outside the finished body, is inserted into the mould used for the manufacture of the closure device by means of an appropriate, eg. conical, core element which may by means of protruding pins or wall elements be designed to maintain an end part of the woven or non-woven material distended in order to obtain the three-dimensional bond with the moulded material, and creates a tightening between the core element and the mould.

The tampon or closure device according to the invention can in particular be used as anal plug for the relief of anorectal incontinence, as a closure device for stomal orifices such as known per se from EP patent no. 188376 or as urethal or vaginal plug for the relief of urinal incontinence, mainly by women. However, the invention is not limited to these fields of application, but is also convenient in connections with devices where no closure device is primarily intended, but which are used for eg. medication as known from several of the before-mentioned publications.

The outer geometrical form and size of the tampon or closure device will of course depend on the purpose of application and in which body canal it is to be used.

Figure 2:
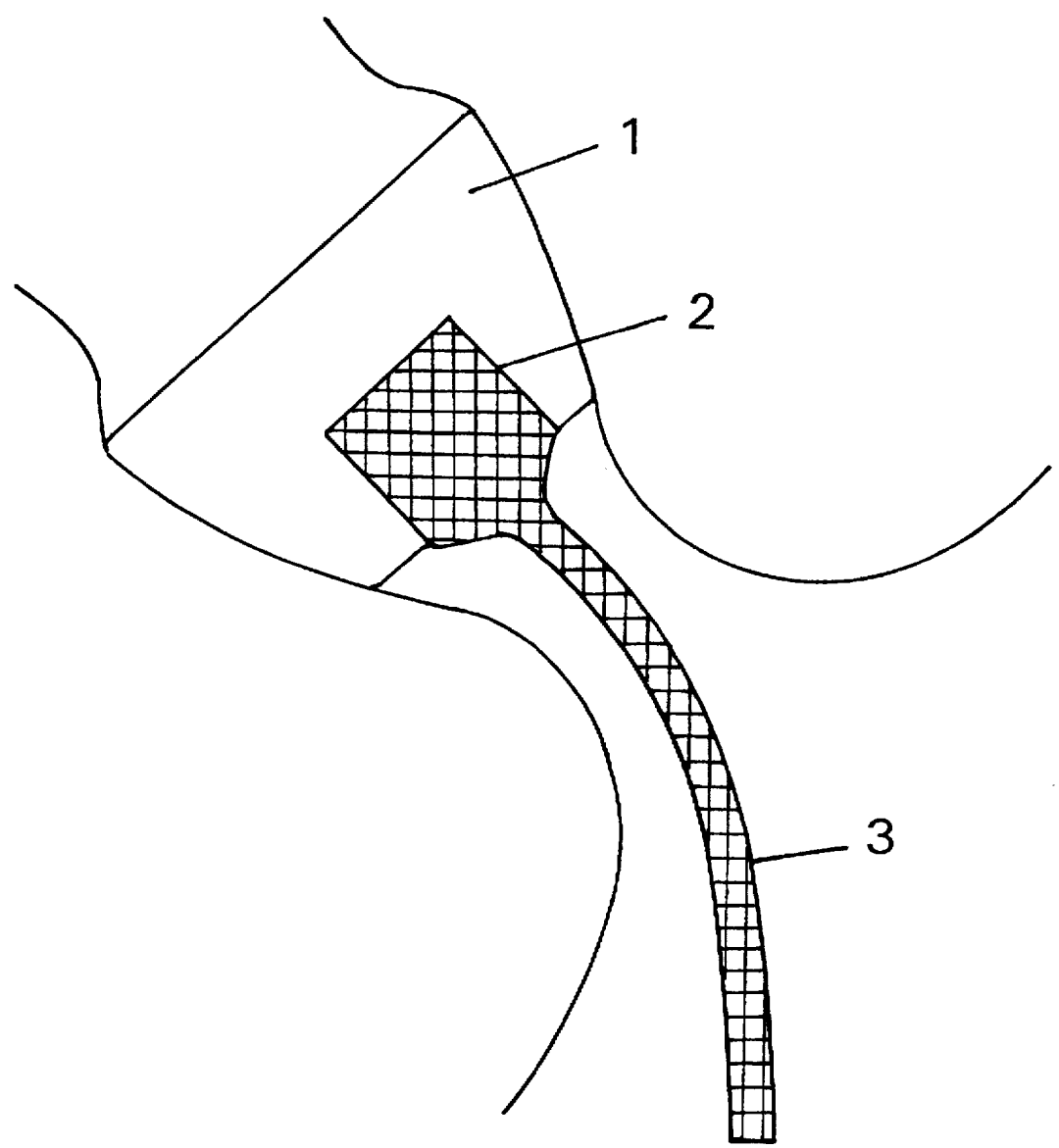

In the following the invention will be explained in detail with referent to the schematic drawing, where FIGS. 1 and 2 show sectional views of an embodiment of a tampon or closure device according to the invention meant for use as an anal plug in a compressed insertion state and an expanded state of use.

The shown anal plug consists of a moulded body 1, preferably of foam polyurethane. As shown in FIG. 1, in order to facilitate the insertion, the body 1 when inserted is compressed to a cross-sectional dimension which does not exceed the cross-dimensions of the body canal in question, here anus, in normal distended state. The plug 1 is retained in this compressed state by means of a surrounding coating 4 of a material, eg. a hydrocolloid, which upon insertion in anus is dissolved and thus permits expansion of the body to the form in which it is manufactured when moulded. Expansions measured by the diameter may lie within the area of 50–400% depending on the character and the application field of the material.

In order to enable the withdrawal of the plug in the state shown in FIG. 2, the device is provided with a handle means protruding outside the moulded body 1 which handle means according to the invention comprises an anchor part 2 consolidated in the moulded body 1 and a handle part 3 in integrated connection herewith.

In the shown embodiment, the handle means in its entirety is designed as a stocking of gauze or a like woven or non-woven material, preferably fabric or plastic. An end part of the stocking forming the anchor part 2 is encapsulated in the moulded body 1 by insertion into the mould used for its manufacture by means of a core element which is designed, eg. with protruding pins, in such a way that during the subsequent foaming process of the moulding material, it maintains the anchor part 2 distended and available for contact with the moulding material both on the exterior and on the interior.

Thereby is obtained a very strong bonding of the anchor part 2 and the moulded material in the body 1 such that a moulding material with a relatively low breaking strength may be used without risk of tearing in connection with the withdrawal.

The moulding material can thus be selected in order to optimize other use properties such as the elastic memory ability necessary for the expansion as well as absorbency, permeability, toxity, etc.

We claim:

1. A tampon or closure device for insertion into an external opening of an artificial or natural body canal of an animal or human being, comprising a resilient compressed plug-like body of a moulded material, said body having a longitudinal direction and being expandable to a cross-sectional dimension ensuring closure of said body canal when inserted in said opening with said longitudinal direction extending longitudinally in said canal, said body being provided with a withdrawal handle means protruding from the body and connected with an anchor part encapsulated in the body and having a relatively large bearing face against the surrounding moulded material of the body, said handle means and anchor part being made from a material with a knitted structure, to provide a three-dimensional bond to the moulded material of said body, the anchor part being designed as a soft flexible element oriented in said longitudinal direction.

2. A tampon or closure device as claimed in claim 1, wherein said anchor part is designed as a relatively short element of woven or non-woven material.

3. A tampon or closure device as claimed in claim 2, wherein said non-woven material is fabric or plastic.

4. A tampon or closure device as claimed in claim 1, wherein said anchor part and the handle means are of gauze.

5. A tampon or closure device as claimed in claim 1, said device being a human anal closure device.

6. A tampon or closure device as claimed in claim 1, said device being a urethral or vaginal closure device for human females.

7. A tampon or closure device as claimed in claim 4, wherein said anchor part and the handle means are integral.

8. A tampon or closure device as claimed in claim 7, wherein said resilient compressed plug-like body has a coating of hydrocolloid.

* * * * *